United States Patent [19]
Dobrin et al.

[11] Patent Number: 5,718,698
[45] Date of Patent: *Feb. 17, 1998

[54] ABSORBENT ARTICLE HAVING BREATHABLE SIDE PANELS

[75] Inventors: George Christopher Dobrin; Karen Marie Davis, both of Cincinnati, Ohio

[73] Assignee: The Procter & Gamble Company, Cincinnati, Ohio

[*] Notice: The term of this patent shall not extend beyond the expiration date of Pat. No. 5,571,096.

[21] Appl. No.: 688,621

[22] Filed: Jul. 30, 1996

Related U.S. Application Data

[63] Continuation of Ser. No. 530,036, Sep. 19, 1995, Pat. No. 5,571,096.

[51] Int. Cl.⁶ .............................. A61F 16/15; A61F 13/20
[52] U.S. Cl. ........................ 604/383; 604/385.1; 604/393
[58] Field of Search .................. 604/358, 367, 604/370, 373, 383, 385.1, 393, 394, 396, 402

[56] References Cited

U.S. PATENT DOCUMENTS

| | | |
|---|---|---|
| 3,426,754 | 2/1969 | Bierenbaum . |
| 3,881,489 | 5/1975 | Hartwell . |
| 3,989,867 | 11/1976 | Sisson . |
| 4,014,341 | 3/1977 | Karami . |
| 4,306,559 | 12/1981 | Nishizawa et al. . |
| 4,324,246 | 4/1982 | Mullane et al. . |
| 4,341,216 | 7/1982 | Obenour . |
| 4,341,217 | 7/1982 | Ferguson et al. . |
| 4,342,314 | 8/1982 | Radel et al. . |
| 4,395,215 | 7/1983 | Bishop . |
| 4,681,578 | 7/1987 | Anderson et al. . |
| 4,681,793 | 7/1987 | Linman et al. . |
| 4,747,991 | 5/1988 | Bishop . |
| 4,795,454 | 1/1989 | Dragoo . |
| 4,872,871 | 10/1989 | Proxmire et al. . |
| 4,887,602 | 12/1989 | O'Leary . |
| 4,900,317 | 2/1990 | Buell . |
| 4,908,026 | 3/1990 | Sukiennik et al. . |
| 5,069,678 | 12/1991 | Yamamoto et al. . |
| 5,085,654 | 2/1992 | Buell . |
| 5,098,423 | 3/1992 | Pieniak et al. . |
| 5,158,819 | 10/1992 | Goodman, Jr. et al. . |
| 5,527,302 | 6/1996 | Endres et al. . |
| 5,571,096 | 11/1996 | Dobrin et al. ..................... 604/383 |
| B1 4,636,207 | 11/1989 | Buell . |

FOREIGN PATENT DOCUMENTS

| | | |
|---|---|---|
| 0 477 802 A1 | 4/1992 | European Pat. Off. . |
| 2 268 389 A | 1/1994 | United Kingdom . |
| 2 295 322 A | 5/1996 | United Kingdom . |
| WO 95/17867 | 7/1995 | WIPO . |

OTHER PUBLICATIONS

Abstract of FR 2699812 Jul. 1, 1994.

*Primary Examiner*—P. Zuttarelli
*Attorney, Agent, or Firm*—David M. Weirich; Steven W. Miller; Jacobus C. Rasser

[57] ABSTRACT

A disposable absorbent articles having breathable side panels. The disposable absorbent article preferably comprises a containment assembly including a topsheet, a backsheet and an absorbent core disposed between the topsheet and the backsheet. The absorbent core has a pair of opposing longitudinal edges, an inner surface and an outer surface. The backsheet has a garment-facing surface, a body-facing surface, a central region and an outer region. The backsheet preferably further includes at least three distinct zones, a pair of apertured zones comprising apertures and a non-apertured zone. The apertured zones preferably include at least a portion of the outer region of the backsheet and extend laterally outwardly form each of the longitudinal edges. The non-apertured zone preferably comprises the central region and is juxtaposed the outer surface of the absorbent core. The disposable absorbent article preferably further comprises a liquid and air pervious outer cover joined with the garment-facing surface of the backsheet to form a breathable laminate in the apertured zones. In preferred embodiments, a side panel extends laterally outwardly from each of the longitudinal edges of the absorbent core, each of the side panels comprising at least a portion of the laminate such that the side panels are breathable.

19 Claims, 3 Drawing Sheets

ABSORBENT ARTICLE HAVING BREATHABLE SIDE PANELS

This is a continuation of application Ser. No. 08/530,036, filed on Sep. 19, 1995 now U.S. Pat. No. 5,571,096.

FIELD OF INVENTION

The present invention relates generally to disposable absorbent articles such as disposable diapers and, more particularly, to disposable absorbent articles having breathable side panels.

BACKGROUND OF THE INVENTION

Infants and other incontinent individuals wear disposable absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. It is also known that the exterior of disposable diapers can be covered with a flexible, liquid and vapor impervious sheet to prevent any absorbed liquid from passing through the diaper and soiling adjacent articles such as clothing, bedding and the like. These outer covers, generally referred to as backsheets, are often constructed from fluid impervious films such as polyethylene. Although such backsheets do prevent liquid from passing through the diaper, they also can make the diaper feel hot and uncomfortable to wear because of their impermeability to air and/or moisture.

Backsheets which are pervious to vapor are generally known as breathable backsheets and have been described in the art. In general, these backsheets are intended to allow the passage of vapor through them while retarding the passage of liquid. For example, U.S. Pat. No. 3,156,242 issued to Crowe, Jr. on Nov. 10, 1964 teaches the use era microporous film as a breathable backsheet. U.S. Pat. No. 3,881,489, issued to Hartwell on May 6, 1975, teaches a breathable backsheet comprising in combination two layers, the first of which is a low void volume perforated thermoplastic film and the second of which is a porous high void volume hydrophobic tissue. U.S. Pat. No. 3,989,867 issued to Sisson on Nov. 2, 1976 teaches a breathable backsheet provided with tapered hollowed bosses which prevent the passage of liquids while allowing vapors to pass readily therethrough.

While these backsheets do provide improvements over the impermeable backsheets of the prior art, they can be relatively expensive and/or difficult to manufacture, especially at high speeds. Often, numerous layers of materials or coatings are needed to provide breathable backsheets capable of containing liquids that may be absorbed by the diaper. Further, in some cases, the breathable backsheets may not effectively contain liquid, especially when the diaper is subjected to the normal forces created by the movements of the wearer.

Therefore, it is an object of the present invention to provide a disposable absorbent article having good containment characteristics while having breathable side panels to ensure comfort for the wearer.

It is a further object of the present invention to provide a disposable absorbent article having a backsheet comprising apertured and non-apertured zones, the non-apertured zone juxtaposed the absorbent core and the apertured zone(s) extending outwardly from the non-apertured zone to form at least a portion of the side panel(s) of the disposable absorbent article.

It is yet another object of this invention to provide a disposable absorbent article having a backsheet comprising apertured and non-apertured zones, wherein tho backsheet further comprises a vapor pervious and/or liquid pervious nonwoven web which provides the garment-facing surface of the backsheet a cloth-like feel.

It is still another object of the present invention to provide a disposable absorbent article having good containment and breathability characteristics that is economical and easy to manufacture at high speeds.

SUMMARY OF THE INVENTION

The present invention is directed to disposable absorbent articles having breathable side panels. The disposable absorbent article preferably comprises a containment assembly including a topsheet, a backsheet and an absorbent core disposed between the topsheet and the backsheet. The absorbent core has a pair of opposing longitudinal edges, an inner surface and an outer surface. The backsheet has a garment-facing surface, a body-facing surface, a central region and an outer region. The backsheet preferably further includes at least three distinct zones, a pair of apertured zones comprising apertures and a non-apertured zone. The apertured zones preferably include at least a portion of the outer region of the backsheet and extend laterally outwardly form each of the longitudinal edges. The non-apertured zone preferably comprises the central region and is juxtaposed the outer surface of the absorbent core. The disposable absorbent article preferably further comprises a liquid and air pervious outer cover joined with the garment-facing surface of the backsheet to form a breathable laminate in the apertured zones. In preferred embodiments, a side panel extends laterally outwardly from each of the longitudinal edges of the absorbent core, each of the side panels comprising at least a portion of the laminate such that the side panels are breathable.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, and the like.

Figure 1:
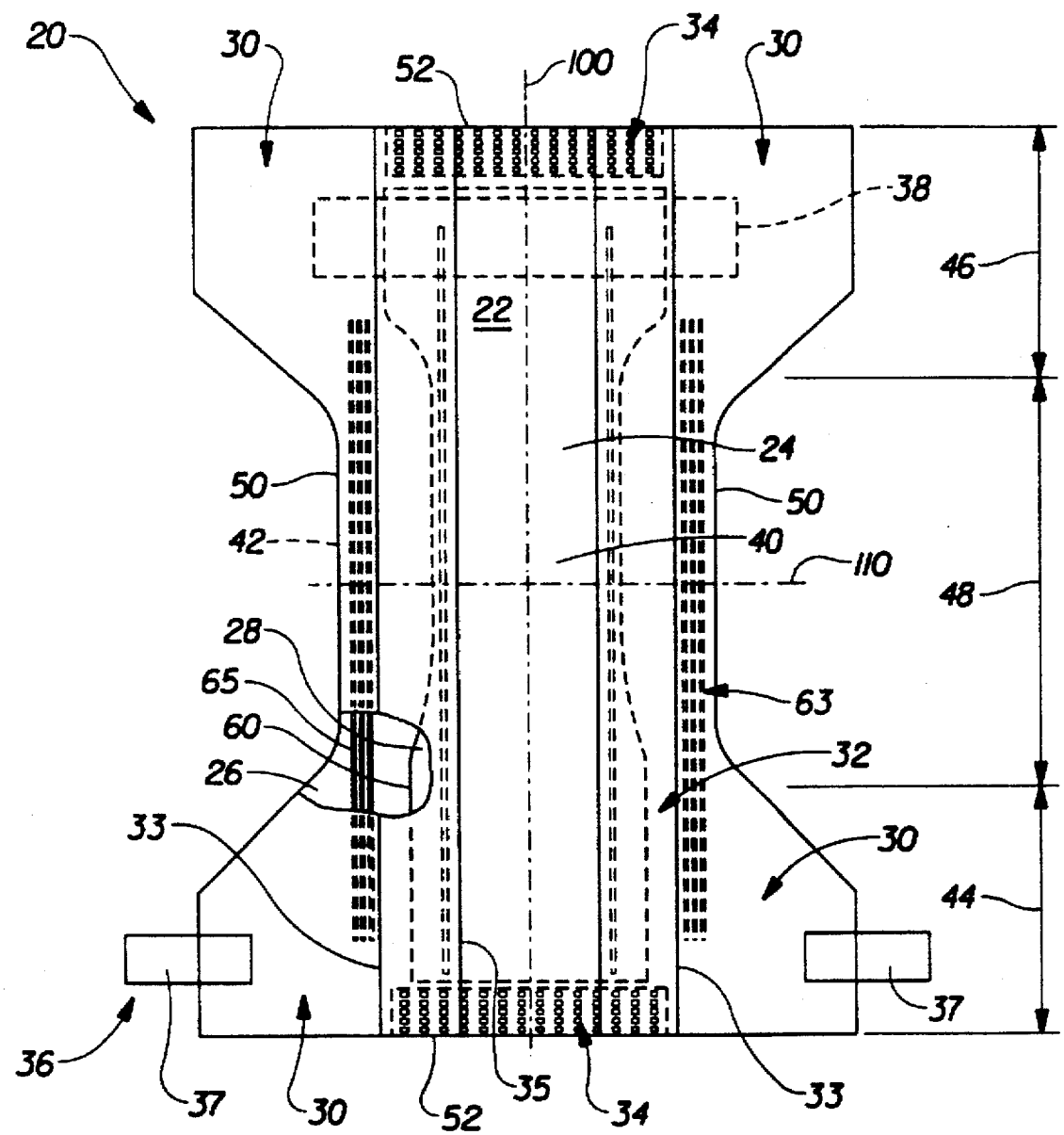
FIG. 1 is a plan view of a disposable diaper embodiment of the present invention having portions cut away to reveal underlying structure, the inner surface of the diaper is facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces the wearer, the inner surface 40, facing the viewer. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The absorbent core 28 has a pair of opposing longitudinal edges 60, an inner surface 62 and an outer surface 64. The diaper preferably further comprises side panels 30; elasticized leg cuffs 32; elasticized waistbands 34; and a fastening system 36 preferably comprising a pair of securement members 37 and a landing member 38.

The diaper 20 is shown in FIG. 1 to have an inner surface 40 (facing the viewer in FIG. 1), an outer surface 42 opposed to the inner surface 40, a rear waist region 44, a front waist region 46 opposed to the rear waist region 44, a crotch region 48 positioned between the rear waist region 44 and the front waist region 46, and a periphery which is defined by the outer perimeter or edges of the diaper 20 in which the side edges are designated 50 and the end edges are designated 52. The inner surface 40 of the diaper 20 comprises that portion of the diaper 20 which is positioned adjacent to the wearers body during use (i.e., the inner surface 40 generally is formed by at least a portion of the topsheet 24 and other components joined to the topsheet 24). The outer surface 42 comprises that portion of the diaper 20 which is positioned away from the wearer's body (i.e., the outer surface 42 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 44 and the front waist region 46 extend from the end edges 52 of the periphery to the crotch region 48.

The diaper 20 also has two centerlines, a longitudinal centerline 100 and a transverse centerline 110. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The containment assembly 22 of the diaper 20 is shown in FIG. 1 as comprising the main body (chassis) of the diaper 20. The containment assembly 22 preferably comprises a topsheet 24, a backsheet 26 and an absorbent core 28 having a pair of opposing longitudinal edges 60, an inner surface 62, an outer surface 64. The inner surface 62 generally faces the body of the wearer while the outer surface 64 generally faces away from the body of the wearer. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 preferably comprises the topsheet 24, the backsheet 26 and the absorbent core 28 of the diaper with other features added to form the composite diaper structure.

FIG. 1 shows a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; each of which is incorporated herein by reference.

The absorbent core 28 may be any absorbent member which is generally compressible, conformable, non-irritating to the wearer's skin, and capable of absorbing and retaining liquids such as urine and other certain body exudates. As shown in FIG. 1, the absorbent core 28 has a garment-facing side, a body-facing side, a pair of side edges, and a pair of waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

One embodiment of the diaper 20 has an asymmetric, modified T-shaped absorbent core 28 having ears in the front waist region but a generally rectangular shape in the rear waist region. Exemplary absorbent structures for use as the absorbent core 28 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The topsheet 24 is preferably positioned adjacent the inner surface 62 of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the diaper periphery and are indirectly joined together by directly joining them to the absorbent core 28 by any suitable attachment means.

The topsheet 24 is preferably compliant, soft feeling, and non-irritating to the wearer's skin. Further, the topsheet 24 is preferably liquid pervious permitting liquids (e.g., urine) to readily penetrate through its thickness. A suitable top sheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from liquids which have passed through the topsheet 24 and are contained in the absorbent core 28 (i.e. to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The top sheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. Nos. 4,988,344 entitled "Absorbent Articles with Multiple Layer Absorbent Layers" issued to Reising, et al on Jan. 29, 1991 and 4,988,345 entitled "Absorbent Articles with Rapid Acquiring Absorbent Cores" issued to Reising on Jan. 29, 1991, each of which is incorporated by reference herein.

An alternative preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference.

The backsheet 26 of the present invention is that portion of the diaper 20 which is generally positioned away from the wearer's skin and which prevents the exudates absorbed and contained in the absorbent core 28 from wetting articles which contact the diaper 20 such as bedsheets and undergarments. Thus, the backsheet 26 is preferably impervious to liquids (e.g., urine) and is preferably manufactured from a thin plastic film, although other flexible liquid impervious materials may also be used. (As used herein, the term "flexible" refers to materials which are compliant and will readily conform to the general shape and contours of the human body.) However, the backsheet 26 permits vapors to escape from the diaper 20. A suitable material for the backsheet 26 is a thermoplastic film having a thickness of from about 0.012 mm (0.5 mil) to about 0.051 mm (2.0 mils), preferably comprising polyethylene or polypropylene.

The backsheet 26 of the present invention may comprise a single member such as the film described above, or may comprise a number of materials joined together to form the backsheet 26. For example, the backsheet may have a central region 74 comprising one film or other member and one or more outer regions 76 joined to the central region 74 comprising the same or different films or other materials. In one preferred embodiment, the backsheet 26 comprises a central region 76 comprising a liquid impervious, non-apertured film and two opposing outer regions 76 comprising an air pervious, apertured film. The means by which any portions of such a backsheet are joined my include any means known in the art such as adhesives, heat, pressure, heat and pressure and ultrasonic bonds. Further, the backsheet 26 may comprise any number of layers of material joined together to form a laminate. If the backsheet 26 is a laminate, the layers need not be uniform throughout the backsheet. For example, the central region 74 of the backsheet 26 may comprise more layers or layers of different material than the outer regions 76.

The backsheet 26 is preferably positioned adjacent the outer surface 64 of the absorbent core 28 and is preferably joined thereto by any suitable attachment means known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

Embodiments of the present invention are also contemplated wherein the absorbent core is not joined to the backsheet 26, and/or the topsheet 24 in order to provide greater extensibility in the front waist region 46 and the rear waist region 44. Alternative embodiments are contemplated wherein an additional member, such as a liquid impervious barrier material(s) (not shown), is positioned between the outer surface 64 of the absorbent core 28 and the backsheet 28. Any such barrier member may or may not be joined to the absorbent core 28. Further, the backsheet 26 may or may not be joined to any barrier material(s) that are positioned between the backsheet 26 and the absorbent core 28.

Figure 2:
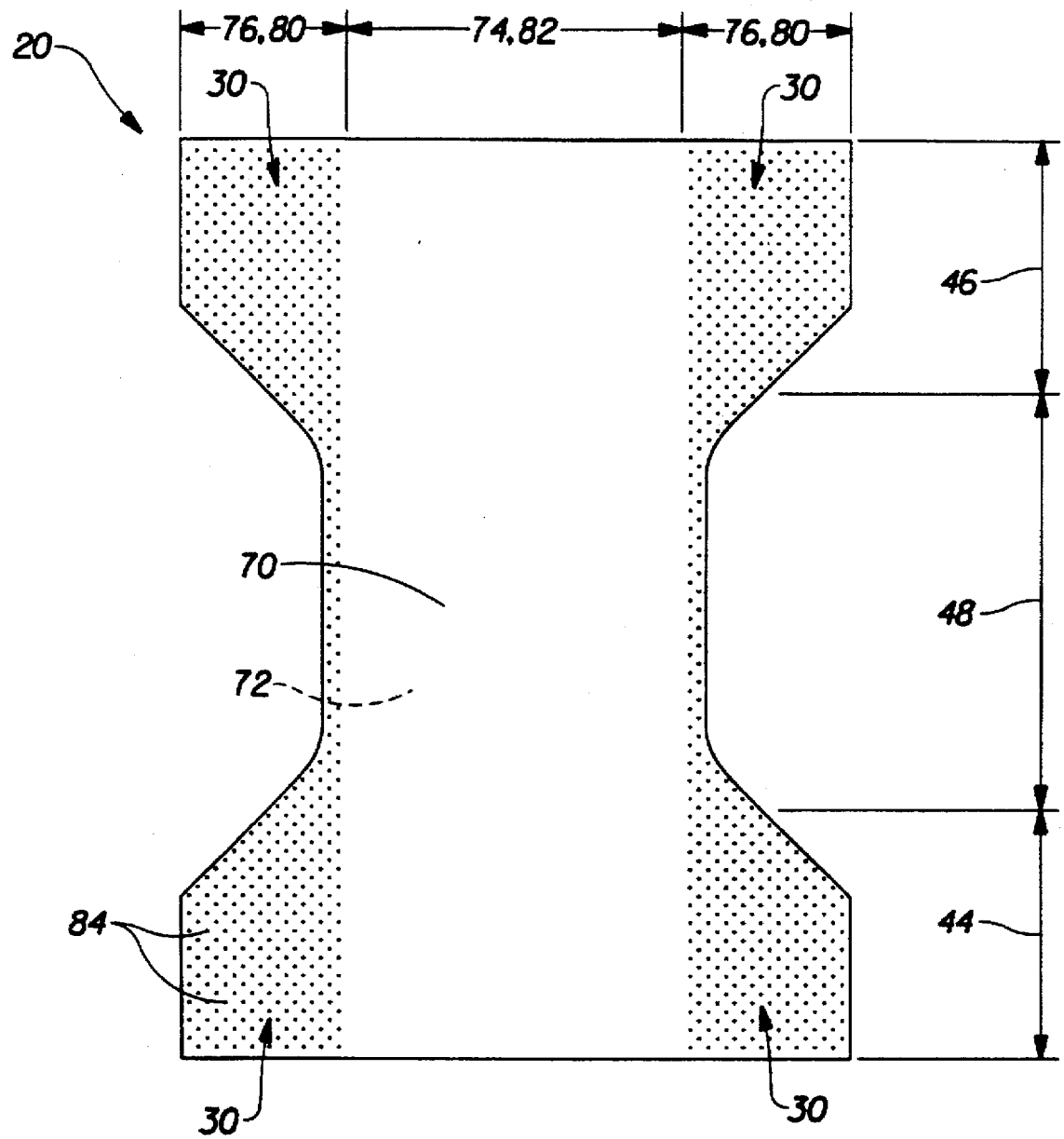
FIG. 2 is a plan view of one embodiment of a backsheet suitable for use in the diaper of the present invention.
Figure 3:
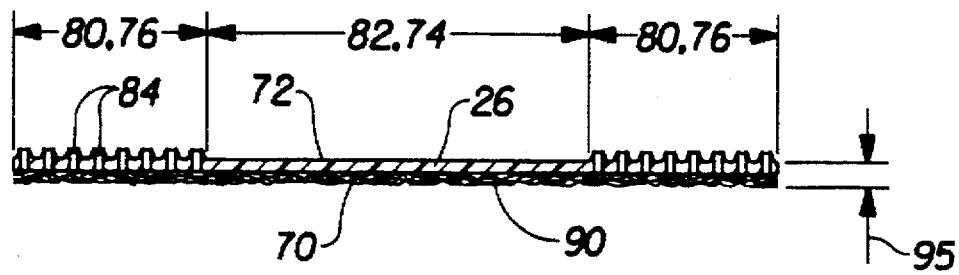
FIG. 3 is an enlarged, cross-sectional view of the backsheet of FIG. 2 shown with a nonwoven web joined thereto.
Figure 4:
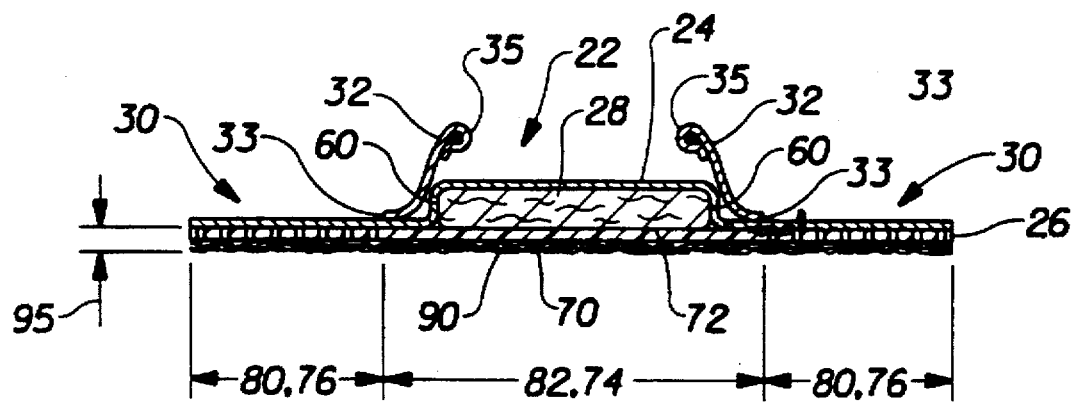
FIG. 4 is an enlarged, cross-sectional view of one embodiment of a disposable absorbent article comprising the backsheet shown in FIGS. 2–3.

The backsheet 26 of the present invention, as shown in FIG. 2, preferably has a body-facing surface 72, a garment-facing surface 70, a central region 74 and at least one outer region 76. Further, the backsheet 26 preferably comprises at least two distinct zones, at least one apertured zone 80 and at least one non-apertured zone 82. In a preferred embodiment, as shown in FIGS. 1 and 4, the backsheet 26 of the present invention comprises at least three distinct zones, a non-apertured zone 82 and two opposing apertured zones 80. The non-apertured zone 82 preferably comprises the central region 74 of the backsheet 26 and is juxtaposed at least a portion of the outer surface 64 of the absorbent core 28. The non-apertured zone 82 provides a liquid impervious structure that contains liquids that have passed into the containment assembly 22. In a preferred embodiment, the non-apertured zone 82 cover the entire outer surface 64 of the absorbent core 28. (As used herein, the term "covers" means that one member is generally, either directly or indirectly in a face to face relationship with another member.) In an especially preferred embodiment, the non-apertured zone 82 not only covers the outer surface 64 of the absorbent core 28, but also extends laterally outwardly to at least any the location at which any barrier cuffs (described below) that may be joined to the diaper 20, such as the proximal edge 33 of the barrier cuff 32. (As used herein, the term "laterally outwardly" refers to a direction away from the longitudinal centerline 100.) This ensures that any liquid absorbed by the core 28 or otherwise deposited into the containment assembly 22 of the diaper 20 will not seep through the apertured zone(s) 80 of the backsheet 26.

The apertured zone(s) 80 of the backsheet 26 of the present invention comprise apertures 84 which permit the passage of vapors and/or liquids. As used herein, the term "aperture" refers to any opening formed in a material that permits at least the passage of vapors. Suitable apertures may comprise slits, perforations, cuts, holes or any other opening or openings that permit the passage of vapor. The apertures 84 may take on any size and shape known in the art. Further, each apertured zone 80 may comprise apertures 84 of differing size and shape. Also, the apertures 84 may be arranged in patterns that are regular or irregular. In a preferred embodiment, the apertured zones 80 comprise apertures having similar dimensions arranged in generally regular patterns. An especially preferred aperture is generally elliptical and has a major axis ranging in length from about 5 mils to about 150 mils. More preferably, the aperture has a major axis length ranging from about 10 mils to about 80 mils; and most preferably, the aperture has a major axis length ranging between about 30 and about 40 mils. Preferred methods for aperturing the apertured zones 80 of the backsheet 26 are described below.

It has been found that the apertured zones 80 can also be described in terms of the density of the apertures and the porosity. As used herein, the term "aperture density" refers to the number of apertures per square inch of material. In preferred embodiments, the aperture density is between about 50 to about 10,000 apertures per square inch and more preferably between about 500 to about 1000 apertures per square inch. The term "porosity" as used herein refers to the air permeability of a material and can be measured according to either of following tests that are well known in the art: ASTM D-737 entitled "Air Permeability of Textile Fabric", or INDA IST 70.0 entitled "Air Permeability". In a preferred embodiment, as measured by the above-referenced ASTM D-737 test, the porosity of the apertured zones is greater than or equal to about 50 cubic feet/minute/square foot of material. More preferably, the porosity is greater than or equal to about 150 cubic feet/minute/square foot of material and most preferably, the porosity is greater than or equal to about 300 cubic feet/minute/square foot of material. Further, embodiments are contemplated wherein the apertured zones 80 have porosity characteristics different from each other or different porosity characteristics within each of the apertured zones 80.

The apertured zone(s) 80 preferably comprise at least a portion of the outer region 76 of the backsheet 26 and preferably extend laterally outwardly from the central region 74 of the backsheet 26 beyond at least one of the longitudinal edges 60 of the absorbent core 28 in at least the rear waist region 44. More preferably, at least one apertured zone 80 extends laterally outwardly from the central region 74 beyond each of the longitudinal edges 60 forming breathable side panels 30 in both the front waist region 46 and the rear waist region 44, as shown in FIGS. 1 and 2. (As used herein, the term "breathable" refers to members that, at a minimum, permit the passage of vapor therethrough. Some breathable members, however, permit the passage of liquids as well as vapors.) In another preferred embodiment, the diaper 20 may also be provided with apertured zones 80 forming breathable side panels 30 that extend from the front waist region 46 through the crotch region 48 and the rear waist region 44 (FIG. 2).

In embodiments of the present invention comprising leg cuffs 32, as described below, the apertured zone(s) 80 may be disposed laterally inwardly or outwardly of the leg cuffs 32. Further, the apertured zone(s) 80 may form a portion of the leg cuffs 32. However, in a preferred embodiment, the apertured zone(s) 80 extend laterally outwardly from the proximal edge 33 of the leg cuff 32. In another preferred embodiment of the present invention, the apertured zone(s) 80 extend laterally outwardly from a location that is laterally outboard of the proximal edge 33 of the leg cuff 32 and laterally inboard of the gasketing cuff 63. Such a configuration provides the diaper 20 with a liquid impervious gasketing seal about the legs of the wearer that prevents liquids from escaping the containment assembly 22 of the diaper 20. In yet another embodiment, the apertured zone(s) 80 extend laterally outwardly from a location laterally outboard of the gasketing cuff 63.

A method of aperturing materials to provide the breathable side panels 30 can readily be selected by those skilled in the art from techniques and designs known to the art. For example, if backsheet 26 is a thermoplastic film (such as common polyethylene film) it can be apertured to provide the apertured zone 80 to a degree which can be described in terms of a dimensionless R value defined as $$R = \frac{D(OA)}{C}$$

wherein D is the average diameter (in centimeters) of the apertures in the film, OA is the total open area of the apertured film expressed as a percentage, and C is the average caliper (or length or height) of the apertures (in centimeters). Normally, when apertures are formed in an elastic film, they take the form of somewhat irregular cones open at both apex and base. Average diameter is the arithmetic average of the diameters of the two openings so formed. Of course, if the apertures are uniformly cut from the film without the usual formation of the cones, caliper will be the film thickness. An apertured film having an R value of between about 2 and about 40, preferably between about 5 and about 25, usually has a vapor transfer rate suitable for use in the present invention. Examples of apertured films and methods for making the films are described in U.S. Pat. No. 3,881,489, issued to Hartwell on May 6, 1975 entitled "Breathable, Liquid Impervious Backsheet For Absorptive Devices"; U.S. Pat. No. 3,989,867, issued to Sisson on Nov. 2, 1976 entitled "Absorptive Devices Having Porous Backsheet"; U.S. Pat. No. 4,341,216, issued to Obenour on Jul. 27, 1982 entitled "Breathable Backsheet For Disposable Diapers"; U.S. Pat. No. 4,342,314 entitled "Resilient Plastic Web Exhibiting Fiber-Like Properties", issued to Radel et al. on Aug. 3, 1982; and U.S. Pat. No. 5,085,654, issued to Buell on Feb. 4, 1992 entitled "Disposable Garment With Breathable Leg Cuffs". (All of these patents are incorporated herein by reference.)

The diaper 20 preferably further comprises an outer cover 90 joined with at least a portion of the garment-facing surface 70 of the backsheet 26 forming a laminate 95. The outer cover 90 preferably comprises a nonwoven web. (However, embodiments are contemplated wherein the outer cover 90 comprises materials such as woven webs, foams, scrims, films, loose fibers, or any other material or combination of materials known in the art that will give the diaper a cloth-like look and/or feel and is at a minimum air permeable.) The outer cover 90 may cover all or substantially all of the garment-facing surface 70 of the backsheet 26, or may cover only discrete predetermined portions. In a preferred embodiment, the nonwoven web of the outer cover 90 covers all or substantially all of the backsheet 26 in order to provide the diaper with a cloth-like look and feel. Further, the outer cover 90 may provide the diaper with a low cost landing zone capable of engaging the hooks of a hook and loop type fastener. (Such a landing zone could be utilized as a portion of a primary fastening system or as a means for disposing of a soiled diaper.) Alternatively, the outer cover 90 may cover only specific portions of the backsheet 26, such as the outer regions 76. In one such embodiment, the outer cover 90 is comprised in the breathable side panels 30. Thus, the outer cover 90 may provide extra strength, bulk, aesthetic appeal or other characteristics desired in the breathable side panels 30. In another embodiment, the nonwoven web 90 is disposed only on the garment-facing surface 70 of the backsheet 26 in the central region 74.

The nonwoven web comprised in the outer cover 90 is preferably liquid and air pervious such that it may be provided juxtaposed the outer regions 76 of the backsheet 26 without substantially decreasing the rate of vapor passage permitted by the apertures 84 located in the breathable side panels 30. The nonwoven web may comprise natural fibers (e.g. cotton or wood fibers), or may comprise fibers of polyethylene, polypropylene, polyester, or any combination of such fibers. Further, the nonwoven may be carded, spunmelt, meltblown or air-through bonded or have any other characteristic or be manufactured in any manner known in the art. Preferably, the nonwoven is comprised of sufficient thermoplastic material to allow for thermal bonding of the material to other components of the diaper. An especially preferred nonwoven is a carded nonwoven made of 100% polypropylene fibers such as FPN 290 manufactured by FiberWeb North America of Simpsonville, S.C. It may be desirable, however, to provide a outer cover 90 that acts to change the perviousness (either vapor or liquid) in certain regions of the breathable side panels 30. Such may be the case in disposable article designs wherein the apertured zone(s) 80 underlie or are otherwise in contact with any portion of the article which may absorb liquids. In such cases it may be desirable to use a hydrophobic nonwoven web to help prevent any leakage of the liquids from the article.

It may also be desirable to provide the disposable article of the present invention with extensibility or elasticity in all or a portion of the side panels 30. (As used herein, the term "extensible" refers to materials that are capable of extending in at least one direction to a certain degree without undue rupture. The terms "elasticity" and "elastically extensible" refer to extensible materials that have the ability to return to approximately their original dimensions after the force that extended the material is removed. As used herein, any material or element described as "extensible" may also be elastically extensible unless otherwise provided.) Extensible side panels 30 provide a more comfortable and contouring fit by initially conformably fitting the diaper to the wearer and sustaining this fit throughout the time of wear well passed when the diaper has been loaded with exudates since the side panels allow the sides of the diaper to expand and contract. Extensible side panels 30 further provide more effective application of the diaper 20 since even if the diaperer pulls one side panel 30 farther than the other during the application (asymmetrically), the diaper 20 will "self-adjust" during wear. While the extensible side panels 30 may be constructed in a number of configurations, examples of diapers with extensible side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and in U.S. Pat. No. 5,151,092 issued to Buell et al. on Sep. 29, 1992; each of which are incorporated herein by reference.

The extensible side panels 30, or any other elements of the diaper 20 in which extensibility or elasticity is desirable such as the waistbands 34 may comprise materials that have been "prestrained", or "mechanically prestrained" (i.e., subjected to some degree of localized pattern mechanical stretching to permanently elongate the material), or structure elastic-like webs (SELF), as described below. The materials may be prestrained using deep embossing techniques as are known in the art. Alternatively, the materials may be prestrained by directing the material through an incremental mechanical stretching system as described in U.S. Pat. No. 5,330,458 entitled "Absorbent Article With Elastic Feature Having A Portion Mechanically Prestrained" issued to Buell et al., on Jul. 19, 1994. The materials are then allowed to return to their substantially untensioned condition, thus forming a zero strain stretch material that is extensible, at least up to the point of initial stretching. Examples of zero strain materials are disclosed in U.S. Pat. No. 2,075,189 issued to Galligan on Mar. 30, 1937; U.S. Pat. No. 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

Alternatively, the extensible side panels 30 or any portions of the side panels 30 or the materials included in the side panels or any other element of the diaper 20 in which extensibility is desirable may comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the mateiaial is in an untensioned condition. The region exhibiting the longer surface-pathlength includes one or more deformations which extend beyond the plane of the other region. The SELF web exhibits at least two significantly different stages on controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web so exhibits second resistive forces to further elongation. The total resistive forces to elongation are higher than the first resistive forces to elongation provided by the first region. SELF webs suitable for the present invention and the method for making such webs are more completely described in the co-pending, commonly assigned U.S. patent application Ser. No. 08/203,456, which has been allowed, entitled "Absorbent Article With Multiple Zone Structural Elastic-Like Film Web Extensible Waist Feature" filed by Donald C. Roe, et al. on Feb. 24, 1994; and in the co-pending, commonly assigned U.S. patent application Ser. No. 08/203,087 entitled "Web Materials Exhibiting Elastic-Like Behavior" filed by Charles W. Chappell, et al. on Feb. 28, 1994, which are incorporated herein by reference.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment. (Each of these patents are incorporated herein by reference.)

While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff comprising a barrier flap and a spacing element such as described in the above-referenced U.S. Pat. No. 4,909,803. In a preferred embodiment, the elasticized leg cuff 32 additionally comprises an elastic gasketing cuff 63 with one or more elastic strands 65, positioned outboard of the barrier cuff such as described in the above-referred U.S. Pat. No. 4,695,278. Further, as shown in FIG. 4, the elasticized leg cuff 32 preferably has a proximal edge 33 and a distal edge 35. The distal edge 35 of the elasticized leg cuff 32 is that part of the elasticized leg cuff 32 which is spaced away from the chassis 22 of the diaper when the diaper 20 is being worn. The proximal edge 33 is that part of the elasticized leg cuff 32 which is joined to the chassis 22 of the diaper 20. The proximal edge 33 is generally located laterally inboard of the periphery of the diaper 20. A portion of the elasticized leg cuff 32, however, may extend laterally outwardly from the proximal edge 33 such that the material covers at least a portion of the outer region 76 of the backsheet 26. (not shown). An example of an elasticized cuff 32 having a portion extending laterally outwardly over most or all of the outer region 76 of the backsheet 26 is described in the above-referenced U.S. Pat. No. 4,795,454 issued to Dragoo, which is hereby incorporated by reference herein.

The diaper 20 preferably further comprises an elasticized waistband 34 that provides improved fit and containment. The elasticized waistband 34 is that portion or zone of the diaper 20 which is intended to elastically expand and contract to dynamically fit the wearer's waist. The elasticized waistband 34 preferably extends longitudinally outwardly from at least one of the waist edges of the absorbent core 28 and generally forms at least a portion of the end edge of the diaper 20. Disposable diapers are generally constructed so as to have two elasticized waistbands, one positioned in the rear waist region and one positioned in the from waist region, although diapers can be constructed with a single elasticized waistband. Further, while the elasticized waistband 34 or any of its constituent elements can comprise a separate element affixed to the diaper 20, the elasticized waistband 34 may be constructed as an extension of other elements of the diaper such as the backsheet 26 or the topsheet 24, preferably both the backsheet 26 and the topsheet 24. Embodiments are also contemplated wherein the elasticized waistband 34 comprises apertures, as described above, to provide breathability in the waist regions. The elasticized waistband 34 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell; each of these references being incorporated herein by reference.

The diaper 20 also comprises a fastening system 36 which forms a side closure which maintains the rear waist region 44 and the front waist region 46 in an overlapping configuration such that lateral tensions are maintained around the circumference of the diaper to maintain the diaper on the wearer. Exemplary fastening systems are disclosed in U.S. Pat. No. 3,848,594 issued to Buell on Nov. 19, 1974; U.S. Pat. No. 4,662,875 issued to Hirotsu and Robertson on May 5, 1987; U.S. Pat. No. 4,869,724 issued to Scripps on Sep. 26, 1989; U.S. Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrell on Aug. 7, 1990; and U.S. Pat. No. 5,326,612 entitled "Nonwoven Female Component For Refastenable Fastening Device And Method of Making the Same" issued to David J. K. Goulait on Jul. 5, 1994. Each of these patents are incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a front waist region, a rear waist region, a crotch region located between lid front waist region and said rear waist region, a pair of opposed side edges, a first edge located in said front waist region and a second end edge rear waist region, the absorbent article comprising:
    a containment assembly comprising an absorbent having a pair of opposing longitudinal edges, an inner surface and an outer surface;
    a topsheet adjacent at least a portion of said absorbent core; and
    a laminate comprising a backsheet and an air pervious outer cover, at least a portion of said backsheet being joined with said top sheet, said backsheet being positioned between said absorbent core and said air pervious outer cover, said backsheet having a garment-facing surface, body-facing surface, a central region, two apertured zones and a non-apertured zone; said non-apertured zone comprising said central region and being juxtaposed at least a portion of said outer surface of said absorbent core; said apertured zones extending outwardly from said central region beyond at least one of said longitudinal edges of said absorbent core; at least a portion of each said apertured zone comprising apertures in said backsheet; a portion of said garment-facing surface of said backsheet being joined with a portion of said outer cover juxtaposed said apertured portion of said apertured zones.

2. The absorbent article of claim 1 wherein said outer cover comprises a nonwoven web.

3. The absorbent article of claim 1 wherein said outer cover is juxtaposed the entire garment-facing surface of said backsheet.

4. An absorbent article having a front waist region, a rear waist region, a crotch region located between said front waist region and said rear waist region, a periphery defined by a pair of opposed side edges, a first end edge located in said front waist region and a second end edge located in said rear waist region, the absorbent article comprising:
    a containment assembly comprising a topsheet, a backsheet and an absorbent core disposed between said topsheet and said backsheet, said absorbent core having a pair of opposing longitudinal edges, an inner surface and an outer surface; a pair of barrier cuffs each having a proximal edge joined to said containment assembly laterally outboard of said opposing longitudinal edges of said absorbent core in at least said crotch region and a distal edge; said backsheet having a garment-facing surface, a body-facing surface, a central region; said backsheet comprising at least three distinct zones, a non-apertured zone comprising said central region and being juxtaposed at least a portion of said outer surface of said absorbent core and a pair of apertured zones comprising apertures, one of said apertured zones extending laterally outwardly from said proximal edge of each said leg cuff;
    an air pervious outer cover joined with at least a portion of said garment-facing surface of said backsheet in at least said apertured zones to form a laminate.

5. The absorbent article of claim 4 wherein said outer cover comprises a nonwoven web.

6. The absorbent article of claim 4 wherein said outer cover is juxtaposed the entire garment-facing surface of said backsheet.

7. The absorbent article of claim 4 wherein said leg cuffs comprise said laminate.

8. The absorbent article of claim 4 wherein said laminate is elastically extensible.

9. The absorbent article of claim 4 wherein said laminate comprise a structural elastic-like film.

10. The absorbent article of claim 4 wherein said backsheet comprises a formed film.

11. The absorbent article of claim 4 wherein said proximal edges of said barrier cuff are disposed laterally outboard of said longitudinal edges of said absorbent core in at least a portion of said front waist region, said crotch region and at least a portion of said rear waist region.

12. The absorbent article of claim 2 wherein at least a portion of said nonwoven web is liquid impervious.

13. The absorbent article of claim 5 wherein at least a portion of said nonwoven web is liquid impervious.

14. An absorbent article having a front waist region, a rear waist region, a crotch region located between said front waist region and said rear waist region, a pair of opposed side edges, a first end edge located in said front waist region and a second end edge located in said rear waist region, the absorbent article comprising:
    a containment assembly comprising an absorbent core having a pair of opposing longitudinal edges; an inner surface and an outer surface;
    a topsheet adjacent at least a portion of said inner surface of said absorbent core; and
    a laminate comprising a backsheet and an air pervious outer cover, at least a portion of said backsheet being joined with said topsheet, said backsheet being positioned between said absorbent core and said air pervious outer cover, said backsheet having a garment-facing surface and a body-facing surface; said backsheet including apertures located laterally outwardly of at least one of said longitudinal edges of said absorbent core; a portion of said garment-facing surface of said backsheet being joined with at least a portion of said outer cover.

15. The absorbent article of claim 14 wherein said outer cover comprises a nonwoven web.

16. The absorbent article of claim 15 wherein at least a portion of said nonwoven web is liquid impervious.

17. An absorbent article having a front waist region, a rear waist region, a crotch region located between said front waist region and said rear waist region, a pair of opposed side edges, a first end edge located in said front waist region and a second end edge located in said rear waist region, the absorbent article comprising:

- a containment assembly comprising an absorbent core having a pair of opposing longitudinal edges, an inner surface and an outer surface;
- a topsheet adjacent at least a portion of said inner surface of said absorbent core; and
- a laminate comprising a backsheet and an air pervious outer cover, at least a portion of said backsheet being joined with said topsheet, said backsheet being positioned between said absorbent core and air pervious outer cover, said backsheet having a garment-facing surface and a body-facing surface; said backsheet including aperture extending continuously outwardly beyond at least one of said longitudinal edges of absorbent core; a portion of said garment-facing surface of said backsheet being joined with at least a portion of said outer cover.

18. An absorbent article having a front waist region, a rear waist region, a crotch region located between said front waist region and said rear waist region, a pair of opposed side edges, a first end edge located in said front waist region and a second end edge located in said rear waist region, the absorbent article comprising:

- a containment assembly comprising an absorbent core having a pair of opposing longitudinal edges, an inner surface and an outer surface; and
- a laminate comprising a backsheet and an air pervious outer cover, said backsheet being positioned between said absorbent core and said air pervious outer cover, said backsheet having a garment-facing surface and a body-facing surface; said backsheet including apertures extending continuously outwardly beyond at least one of said longitudinal edges of said absorbent core in at least said crotch region; a portion of said garment-facing surface of said backsheet being joined with at least a portion of said outer cover.

19. The absorbent article of claim 18 wherein said apertures extend continuously longitudinally from said end edge in said front waist region through said crotch region to said end edge in said rear waist region.

* * * * *

UNITED STATES PATENT AND TRADEMARK OFFICE
CERTIFICATE OF CORRECTION

PATENT NO.    : 5,718,698
DATED         : February 17, 1998
INVENTOR(S)   : Dobrin et al.

It is certified that error appears in the above-identified patent and that said Letters Patent is hereby corrected as shown below:

Column 1,
Line 36, "era" should read -- of a --.

Column 2,
Line 3, "tho" should read -- the --.

Column 9,
Line 56, "an" should read -- art --.

Column 11,
Line 39, "materaial" should read -- material --.
Line 51, "so" should be deleted.

Column 12,
Line 62, "from" should read -- front --.

Column 13,
Line 36, "lid" should read -- said --.
Line 38, "first edge" should read -- first end edge --.
Line 39, "second end edge rear waist region" should read -- second end edge located in said rear waist region --.

Column 15,
Line 26, "aperture" should read -- apertures --.

Signed and Sealed this

Eighteenth Day of September, 2001

*Attest:*

NICHOLAS P. GODICI
*Attesting Officer*    Acting Director of the United States Patent and Trademark Office